(12) United States Patent
Rosenberg et al.

(10) Patent No.: US 7,407,627 B1
(45) Date of Patent: Aug. 5, 2008

(54) ANALYZER HAVING A ROTATABLE SAMPLE RACK CARRIER

(75) Inventors: Burkard Rosenberg, Horw (CH); Gottlieb Schacher, Lucerne (CH)

(73) Assignee: Roche Diagnostics Corporation, Indianapolis, IN (US)

( * ) Notice: Subject to any disclaimer, the term of this patent is extended or adjusted under 35 U.S.C. 154(b) by 875 days.

(21) Appl. No.: 10/129,882

(22) PCT Filed: Oct. 31, 2000

(86) PCT No.: PCT/EP00/10836

§ 371 (c)(1),
(2), (4) Date: May 10, 2002

(87) PCT Pub. No.: WO01/36981

PCT Pub. Date: May 25, 2001

(30) Foreign Application Priority Data

Nov. 12, 1999 (EP) .................................. 99811041

(51) Int. Cl.
*G01N 35/00* (2006.01)
(52) U.S. Cl. ............................ 422/64; 422/63; 422/65; 422/99; 422/100; 422/101; 436/44; 436/47; 436/48
(58) Field of Classification Search ........... 422/99–101, 422/63–67; 436/180, 44, 47–48
See application file for complete search history.

(56) References Cited

U.S. PATENT DOCUMENTS

| | | | |
|---|---|---|---|
| 4,678,752 A * | 7/1987 | Thorne et al. ............ | 435/287.3 |
| 4,834,944 A | 5/1989 | Wakatake .................... | 422/64 |
| 5,138,868 A | 8/1992 | Long ................................ | 73/1 |
| 5,207,986 A | 5/1993 | Kadota et al. ................ | 422/65 |
| 5,443,791 A * | 8/1995 | Cathcart et al. .............. | 422/65 |
| 5,580,524 A * | 12/1996 | Forrest et al. ................. | 422/63 |
| 5,620,898 A | 4/1997 | Yaremko et al. .............. | 436/45 |
| 5,833,925 A * | 11/1998 | Shu et al. ....................... | 422/63 |
| 6,117,392 A * | 9/2000 | Hanawa et al. ................ | 422/65 |

FOREIGN PATENT DOCUMENTS

| | | |
|---|---|---|
| DE | 197 42 160 | 4/1998 |
| EP | 0 325 101 | 7/1989 |
| EP | 0 806 672 | 11/1997 |
| EP | 0 856 736 | 8/1998 |
| EP | 0 867 724 | 9/1998 |
| EP | 0 889 328 | 1/1999 |

OTHER PUBLICATIONS

Patent Abstracts of Japan, vol. 014, No. 249, May 28, 1990.

* cited by examiner

*Primary Examiner*—Jill Warden
*Assistant Examiner*—Jyoti Nagpaul
(74) *Attorney, Agent, or Firm*—McDonnell Boehnen Hulbert & Berghoff LLP

(57) ABSTRACT

The present invention is directed to an automatic chemical analytical apparatus for analyzing liquid samples. In order to provide a fully automatic transport of sample tubes containing samples to be analyzed, the apparatus includes a sample processing unit, a sample transport arrangement for transporting the sample racks from a rack supply unit to a rotatable sample rack carrier in the sample processing unit and vice versa, and a computer for controlling and coordinating the operation of the sample transport arrangement and an automatic pipetting unit. The sample processing unit includes the automatic pipetting unit and the rotatable sample rack carrier that accommodates a plurality of sample racks. Each sample rack, in turn, accommodates a plurality of sample tubes.

27 Claims, 4 Drawing Sheets

ANALYZER HAVING A ROTATABLE SAMPLE RACK CARRIER

FIELD OF THE INVENTION

The invention concerns an automatic chemical analytical apparatus for analyzing liquid samples.

BACKGROUND OF THE INVENTION

The invention concerns in particular an automatic chemical analytical apparatus comprising an automatic pipetting unit for aspirating a sample portion from a selected sample tube from an array of sample tubes located in a sample tube area, and for delivering said aspirated sample portion to a selected reaction tube from an array of reaction tubes located in a reaction tube area, each sample tube carrying on it an identification readable by a reader device, a plurality of elongated sample racks, each of which has a length axis and is adapted to accommodate a plurality of sample tubes, each sample tube being filled with a sample, each sample rack carrying on it an identification readable by a reader device, a rotatable sample rack carrier located in said sample tube area, said rotatable sample rack carrier being adapted to accommodate a plurality of said sample racks within a space delimited by a circumference, said sample racks being arranged along said circumference with the length axis of each of said sample racks substantially orthogonal to said circumference.

An analytical apparatus of this kind is described in European Patent Specification No. EP 0325101 B1. This document contains no description of any means for automatically transporting sample racks from a rack supply unit to the rotatable sample rack carrier and for positioning the sample racks on that rack carrier or for automatically removing the sample racks from that carrier and transporting them back to the rack supply unit. Therefore, according to EP 0325101 B1, the latter transport and positioning and removing operations have to be done manually.

In order to improve the reliability of the operation of such an analytical apparatus and generally in order to improve the overall performance of such apparatus, it is desirable to avoid as much as possible any manual operations for the transport of the sample tubes.

The aim of the invention is therefore to provide an analyzer of the above mentioned kind wherein the transport of the sample tubes is completely automated.

SUMMARY OF THE INVENTION

According to the invention, this aim is achieved with an automatic analytical apparatus of the above mentioned kind which comprises:

(a) an automatic pipetting unit for aspirating a sample portion from a selected sample tube from an array of sample tubes located in a sample tube area, and for delivering said aspirated sample portion to a selected reaction tube from an array of reaction tubes located in a reaction tube area, each sample tube carrying on it an identification readable by a reader device, said automatic pipetting unit comprising a pipetting needle and means for moving said needle in 3 directions which are orthogonal to each other, (b) a plurality of elongated sample racks each of which has a length axis and accommodates a plurality of sample tubes, each sample tube being filled with a sample, each sample rack carrying on it an identification readable by a reader device, (c) a rotatable sample rack carrier located in said sample tube area, said rotatable sample rack carrier accommodating a plurality of said sample racks within a space delimited by a circumference, said sample racks being arranged along said circumference with the length axis of each of said sample racks substantially orthogonal to said circumference, (d) sample transport means for transporting said sample racks from a rack input device of a rack supply unit to said rotatable sample rack carrier, and for selectively transporting said sample racks from said rotatable sample rack carrier to a rack output device of said rack supply unit, said rack input device and said rack output device each accommodating a plurality of said sample racks, said sample transport means including means for rotating in a step-wise manner said rotatable sample rack carrier, said step-wise rotation comprising rotation intervals and rotation stop intervals, during which said sample rack carrier is at rest, (e) said automatic pipetting unit for aspirating a portion of a sample contained in a selected sample tube located in a selected sample rack carried by said sample rack carrier during a rotation stop interval, and for delivering said aspirated sample portion to a selected reaction tube in said reaction tube area, and (f) means for controlling and coordinating the operation of said sample transport means and said automatic pipetting unit.

The main advantage of an analytical apparatus according to the invention is that it includes means which provide a completely automatic transport of the sample tubes, and that these means makes it possible to attain simultaneously two aims:

on the one hand, to provide such automatic transport at a relatively low cost and with a simple structure which facilitates service work and thereby reduces service expenses, and on the other hand, to coordinate such automatic transport of sample tubes with the necessary sample pipetting operations, and to enable selective random-access to any of the sample tubes in the sample area for carrying out those pipetting operations.

Achievement of these aims contributes to optimizing/increasing the number of samples the analytical apparatus is able to analyze per unit of time. Moreover, according to the invention, the sample racks remain on the rotatable sample rack carrier as long as the analysis of any of the sample tubes contained therein is not yet completed. Thus, the sample rack carrier serves also as a buffer for sample racks, and in this way, the instant invention eliminates the need for a separate sample rack buffer.

Preferred embodiments of the invention are described hereinafter in further detail with reference to the accompanying drawings.

DETAILED DESCRIPTION OF THE INVENTION

Figure 1:
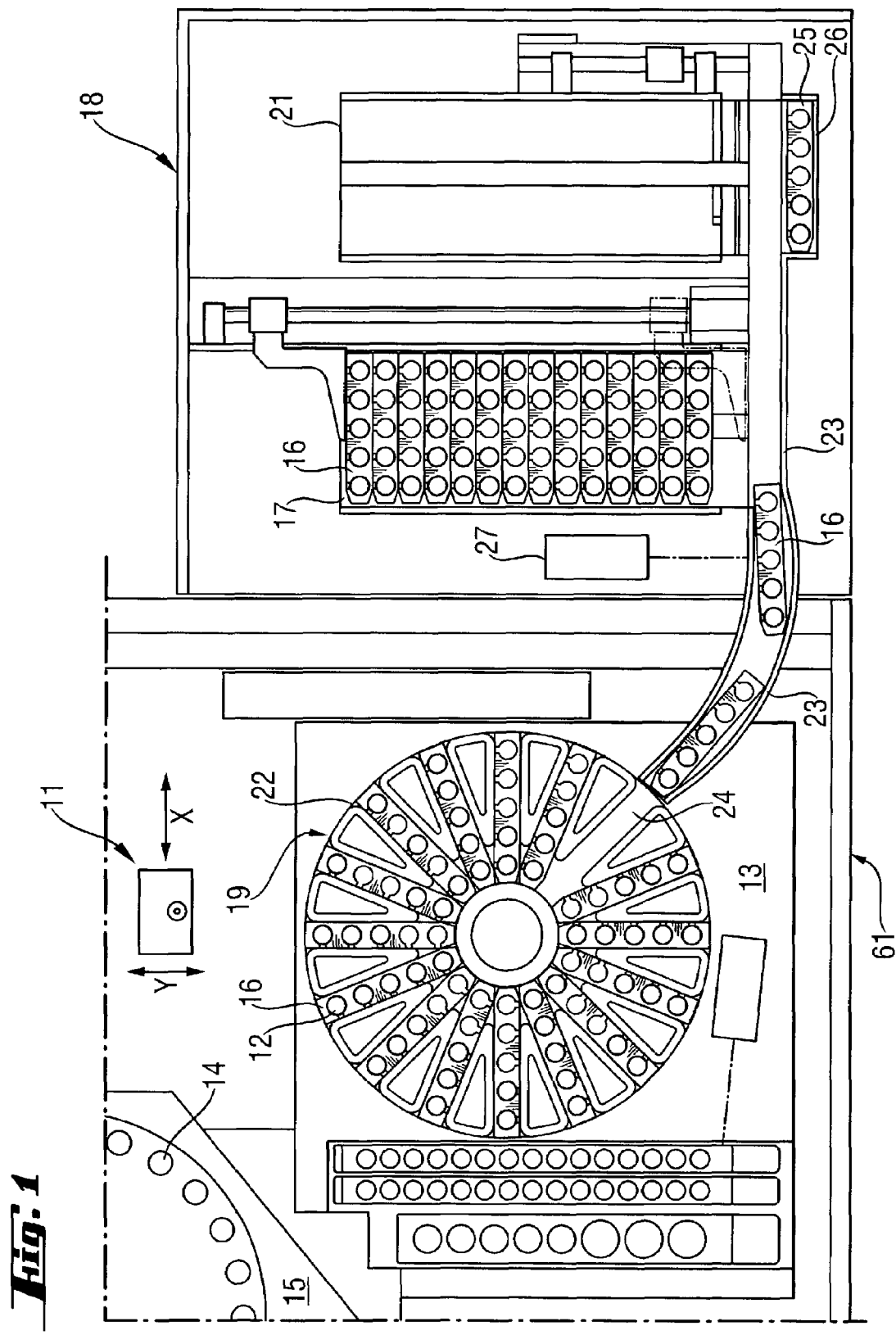
FIG. 1 shows a schematic partial top view of an analyzer system according to the invention.

As shown by FIG. 1, an embodiment of an automatic chemical analytical apparatus according to the invention comprises:

a) a sample processing unit 61 comprising:
an automatic pipetting unit 11, and
a rotatable sample rack carrier 19, adapted to accommodate a plurality of said sample racks 16, each sample rack 16 being adapted to accommodate a plurality of sample tubes 12, b) sample transport means for transporting sample racks 16 from a rack supply unit 18 to rotatable sample rack carrier 19, and for selectively transporting sample racks 16 from rotatable sample rack carrier 19 to rack supply unit 18, and c) means for controlling and coordinating the operation of the sample transport means and automatic pipetting unit 11.

Rack supply unit 18 comprises a rack input device 17 and a rack output device 21. In a preferred embodiment, rack supply unit 18 is located outside sample tube area 13 and comprises a stationary rack input device 17 and a stationary rack output device 21. In a preferred embodiment, rack supply unit 18 is a separate module which is adapted to cooperate with sample processing unit 61 as described hereinafter, but which is not a part of the latter unit. For this purpose, rack supply unit 18 is so configured that sample racks 16 located therein are accessible for transport to and from sample processing unit 61.

A preferred embodiment of automatic pipetting unit 11 comprises a pipetting needle and transport means for moving the pipetting needle in 3 directions X, Y, Z, which are orthogonal to each other. Such a transport system of the pipetting needle enables a random-access to samples contained in sample tubes carried by rotatable sample rack carrier 19.

In a preferred embodiment, sample processing unit 61 comprises a sample tube area for receiving sample tubes to be analyzed and a reaction tube area for receiving reaction tubes where the necessary reactions of the samples with suitable reagents take place.

In a preferred embodiment, the sample tube area 13 includes space reserved for accommodating one or more additional sample tube racks, which are manually positioned on a stationary support. These sample tube racks are not transported by the sample transport means of an analytical apparatus according to the invention.

Automatic pipetting unit 11 is adapted for performing pipetting operations such as e.g. aspirating a sample portion from a selected sample tube 12 of an array of sample tubes 12 located in a sample tube area 13, and for delivering the aspirated sample portion to a selected reaction tube 14 of an array of reaction tubes 14 located in a reaction tube area 15. Automatic pipetting unit 11 is controlled by suitable control means in order to perform such pipetting operations successively with respect to a plurality of sample tubes, and of reaction tubes, respectively. Each sample tube 12 carries on it an identification readable by a reader device 27.

Rotatable sample rack carrier 19 is located in sample tube area 13 and is adapted to accommodate a plurality of sample racks 16 within a space delimited by a circumference 22. Sample racks 16 are arranged along circumference 22 with the length axis of each of sample racks 16 substantially orthogonal to circumference 22, that is, the length axis of each of the sample racks 16 is radially oriented with respect to the axis of rotation of rotatable sample rack carrier 19.

Figure 2:
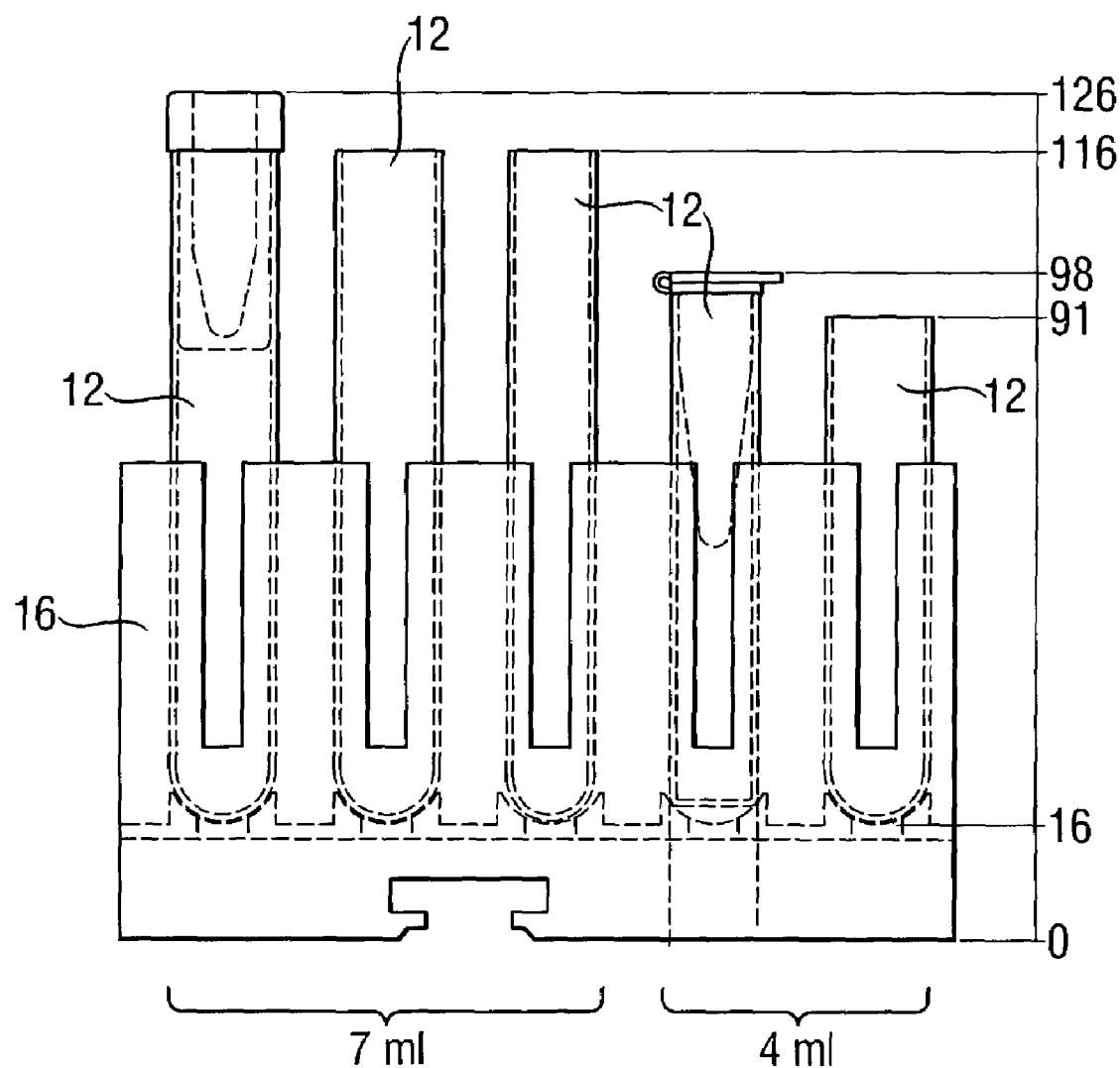
FIG. 2 shows a schematic side view of one of the racks 16 shown by FIG. 1 and of sample tubes 12 contained therein.

As can be appreciated from FIGS. 1 and 2, each sample rack has an elongated shape and a length axis and is adapted to accommodate a plurality of sample tubes 12 each containing a sample to be analyzed.

As shown by FIG. 2, sample tubes 12 can have different sizes, e.g. 4 ml or 7 ml, as indicated for some of the sample tubes. On the right side of FIG. 2, lengths in millimeters are indicated.

Each sample rack 16 carries on it an identification readable by a reader device 27. In a preferred embodiment, sample tubes 12 are arranged substantially in a row along the length axis of sample rack 16.

The sample transport means is adapted for transporting sample racks 16 from a rack input device 17 of rack supply unit 18 to rotatable sample rack carrier 19, and for selectively transporting sample racks 16 from rotatable sample rack carrier 19 to a rack output device 21 of rack supply unit 18. Rack input device 17 and rack output device 21 are each adapted to accommodate a plurality of sample racks 16.

The sample transport means includes means for rotating in a step-wise manner rotatable sample rack carrier 19. This step-wise rotation comprises rotation intervals and rotation stop intervals, during which sample rack carrier 19 is at rest.

In a preferred embodiment, the sample transport means are adapted for transporting sample racks 16 one-by-one from rack input device 17 to rotatable sample rack carrier 19.

In a further preferred embodiment, the sample transport means are adapted for selectively transporting sample racks 16 one-by-one from rotatable sample rack carrier 19 to rack output device 21.

A typical pipetting operation performed by automatic pipetting unit 11 is as follows: aspiration of a portion of a sample contained in a selected sample tube 12 located in a selected sample rack 16 carried by sample rack carrier 19 during a rotation stop interval, and delivery of the aspirated sample portion to a selected reaction tube 14 in reaction tube area 15.

The control means, which control and coordinate the operation of the sample transport means and the automatic pipetting unit 11, include e.g. a computer. The computer receives all necessary information from the different parts that constitute the analytical apparatus, and generates corresponding command signals for controlling automatic pipetting unit 11 and various parts of the sample transport means according to a suitable program. The program provides an optimized operation of the system components which participate in the transport of the sample racks 16 for a predetermined range of number of samples processed by the system by time unit.

In a preferred embodiment, the sample transport means include a transfer line 23 for transporting sample racks from rack supply unit 18 to rotatable sample rack carrier 19 and vice versa, means for moving serially and one-by-one sample racks 16 from rack input device 17 to transfer line 23, means for moving one-by-one sample racks 16 from transfer line 23 to rack output device 21, means for moving one-by-one sample racks 16 from transfer line 23 to rotatable sample rack carrier 19 and vice versa, means for rotating in a step-wise manner rotatable sample rack carrier 19, and a reader device 27 for reading the identification of each sample rack 16 and the identification of each sample tube 16 contained therein during their transport from the rack supply unit 18 to the rotatable sample rack carrier 19.

In a preferred embodiment, the sample transport means further comprise means for moving a sample rack 25 containing at least one sample that requires urgent analysis. The rack 25 is moved from a rack input position 26 for such kind of rack to transfer line 23 in order that such sample rack 25 can be transferred to rotatable sample rack carrier 19 with high priority.

In a preferred embodiment, transfer line 23 is a single transfer line 23 for transporting sample racks 16 in two opposite directions, that is, from rack supply unit 18 to rotatable sample rack carrier 19 and vice versa.

Figure 3:
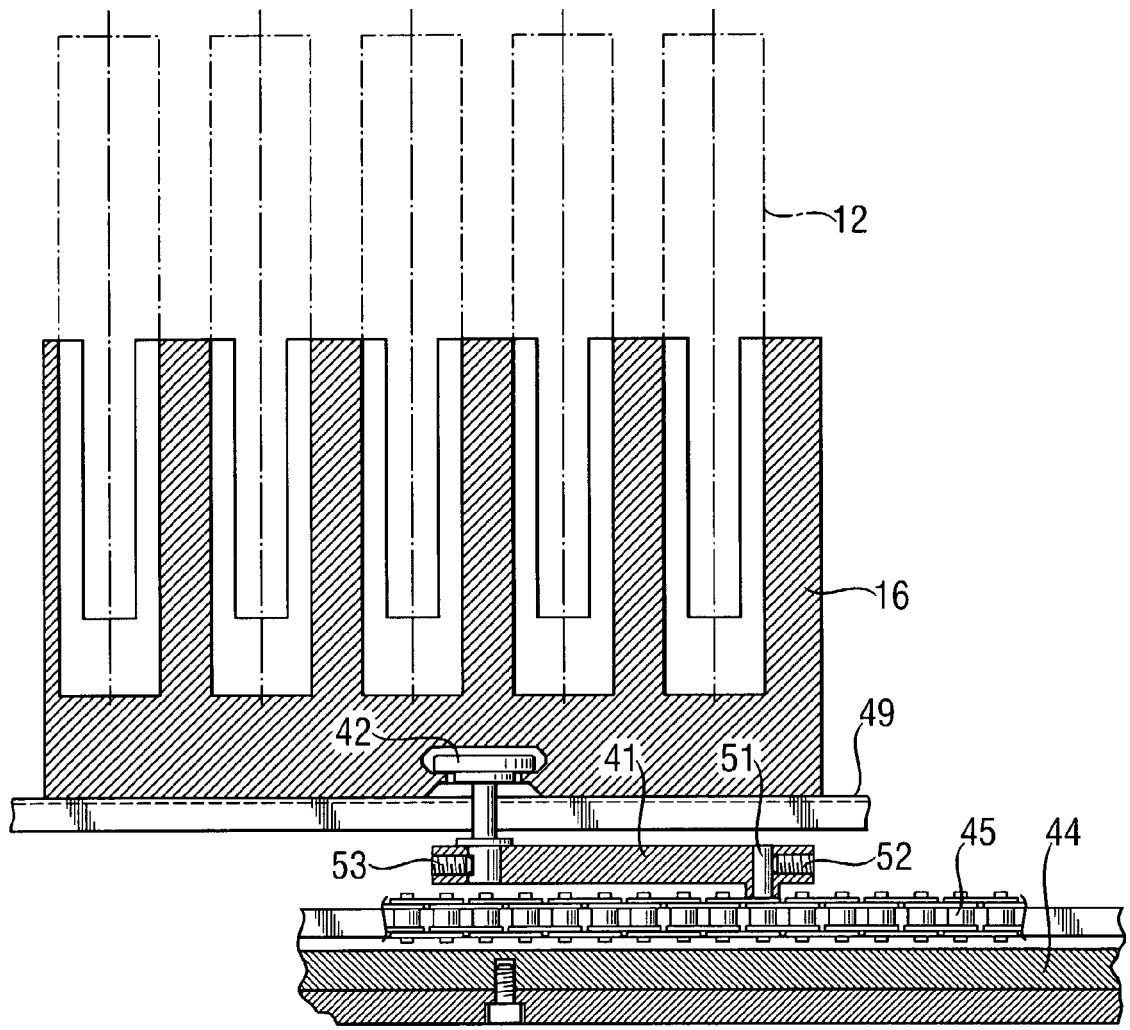
FIG. 3 shows a schematic cross-sectional view of mechanical means for moving a sample rack 16 along transfer line 23 shown by FIG. 1.
Figure 4:
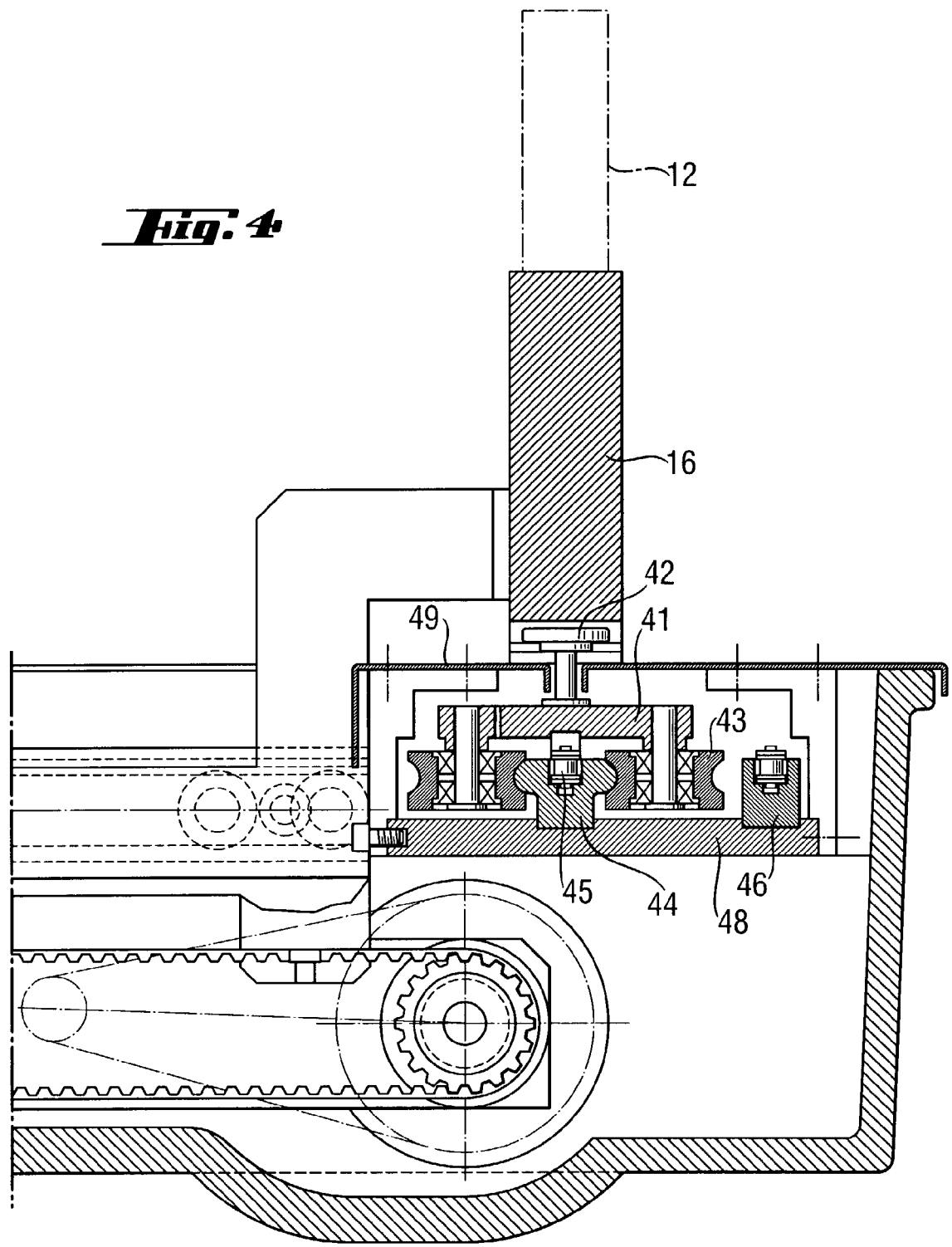
FIG. 4 shows a schematic cross-sectional view of the mechanical means shown in FIG. 3 in a plane perpendicular to the plane of the cross-section represented in FIG. 3.

FIGS. 3 and 4 show schematic cross-sectional views of mechanical components which form part of an embodiment of transfer line 23 described herein as an example. These components cooperate with each other for moving a sample rack 16 along transfer line 23 shown by FIG. 1. As can be appreciated from FIGS. 3 and 4, a sample rack 16 is displaced on a support plate 49. Transport of sample rack 16 in a desired direction is achieved by means of a carriage 41 and a transport chain 45. Carriage 41 is removably connected to sample rack 16 by means of a pin 42. The upper part of a pin 42 of carriage 41 is removably lodged in a corresponding cavity of the bottom wall of sample rack 16.

As shown by FIG. 4, guiding rolls 43 and a guiding rail 44 guide movement of carriage 41. A chain guide 46 guides movement of chain 45. A base plate 48 supports guiding rail 44 and the mechanical components which cooperate with it.

As shown by FIG. 3, a carrier bolt 51 connects carriage 41 to chain 45. Pin 42 is fixed to carriage 41 by means of a set screw 53. Carrier bolt 51 is fixed to carriage 41 by means of a set screw 52.

The means for rotating in a step-wise manner rotatable sample rack carrier 19 include e.g. a D.C. motor and a encoder. This D.C. motor is controlled by the above-mentioned control means.

The means for rotating a step-wise manner rotatable sample rack carrier 19 operate in such a way that the step-wise rotation of rack carrier 19 comprises rotation intervals and rotation stop intervals, during which sample rack carrier 19 is at rest.

The step-wise rotation of rack carrier 19 is performed so that at the end of each rotation step a selected one of the sample racks 16 is aligned with and is ready to be transferred either to transfer line 23 for its transport to rack output device 21 of rack supply unit 18, or to a free position 24 available to receive a sample rack 16 on sample rack carrier 19. The free position 24 is aligned with transfer line 23 for receiving a sample rack 16 arriving to sample rack carrier 19 via transfer line 23. For this purpose, the length axis of the end part of transfer line 23 is preferably radially oriented with respect to the axis of rotation of rotatable sample carrier 19.

Each rotation step includes rotation of sample rack carrier 19 of an angle determined by the control means, e.g. an angle smaller than 180 degrees. The means for rotating rack carrier 19 are so configured that carrier 19 can be rotated in one of two opposite directions, i.e. in clock-wise direction or in a direction opposite thereto.

The means for moving sample racks 16 one-by-one from transfer line 23 to rotatable sample rack carrier 19 and vice versa include means for moving a selected sample rack 16 from transfer line 23 to a free position 24 on sample rack carrier 19, during one of the rotation stop intervals, and for moving a selected sample rack 16 from its position on the sample rack carrier 19 to the transfer line 23, during another one of the rotation stop intervals.

The selection of a sample rack 16 to be removed from rack carrier 19 is made by the control means on the basis of the information available on the status of the analysis operations with respect to every sample tube on carrier 19. Every sample rack 16 remains on rack carrier 19 as long as analysis of a sample tube in that rack has not yet been completed or has to be repeated, because validity of results is deemed to be doubtful. Therefore, rack carrier 19 also performs the function of a buffer. Thus, a separate sample rack buffer is not necessary. When the analysis of all sample tubes in a sample rack 16 is completed, the control means select that rack and provide the necessary commands in order to remove that rack from rack carrier 19 as fast as possible. Therefore, every sample rack 16 remains on rack carrier 19 only during the minimum time interval required for enabling analysis of the samples on that rack.

The identifications carried by the sample tubes 12 and the sample racks 16 are e.g. bar-code labels readable by a bar-code reader 27. In the embodiment shown by FIG. 1, bar-code reader 27 is fixedly disposed in the analyzer and is used to read the bar-code labels of each sample rack and of each sample tube contained on each vessel holder as these components pass before the bar-code reader and cross the reading path thereof during their transport on transfer line 23 from rack input device 17 to sample rack carrier 19.

Numerous modifications and alternative embodiments of an analytical apparatus according to the invention will be apparent to those skilled in the art in view of the foregoing description. Accordingly, this description is to be construed as illustrative only and is for the purpose of teaching those skilled in the art the best mode of carrying out the invention. Details of the apparatus may be varied substantially without departing from the spirit of the invention and the exclusive use of all modifications which come within the scope of the appended claims is reserved.

The invention claimed is:

1. An automatic chemical analytical apparatus for analyzing liquid samples comprising:
   (a) a plurality of elongated sample racks, each of which has a length axis and accommodates a plurality of sample tubes, each sample tube being filled with a sample, each sample tube carrying on it an identification readable by a reader device and each sample rack carrying on it an identification readable by a reader device,
   (b) first sample transport means including a rotatable sample rack carrier located in a sample tube area, said rotatable sample rack carrier accommodating a plurality of said sample racks within a space delimited by a circumference of the carrier, said sample racks being arranged along said circumference with the length axis of each of said sample racks orthogonal to said circumference, said first sample transport means further including means for rotating in a step-wise manner said rotatable sample rack carrier, said step-wise rotation comprising rotation intervals and rotation stop intervals, during which said sample rack carrier is at rest,
   (c) second sample transport means for transporting said sample racks from a rack input device of a rack supply unit to said rotatable sample rack carrier, and for selectively transporting said sample racks from said rotatable sample rack carrier to a rack output device of said rack supply unit, said rack input device and said rack output device each accommodating a plurality of said sample racks, (d) an automatic pipetting unit for aspirating a portion of a sample contained in any sample tube located in any sample rack carried by said sample rack carrier, said aspirating being effected during a rotation stop interval, and for delivering said aspirated sample portion to any reaction tube in a reaction tube area, said automatic pipetting unit comprising a pipetting needle and means for moving said needle in each one of 3 directions (X, Y, Z) which are orthogonal to each other, (e) means for controlling and coordinating the operation of said first sample transport means, said second sample transport means, and said automatic pipetting unit, so that a selected sample is delivered to a selected reaction tube; and (f) computer control means which control the operation of said automatic pipetting unit, said first sample transport means, and said second sample transport means, for minimizing the time interval during which each rack occupies a place on said rotatable sample rack carrier.

2. The apparatus according to claim 1, wherein said second sample transport means transport said sample racks one-by-one from said rack input device to said rotatable sample rack carrier.

3. The apparatus according to claim 1, wherein said second sample transport means selectively transport said sample racks one-by-one from said rotatable sample rack carrier to said rack output device.

4. The apparatus according to claim 1, wherein said rack supply unit is a separate module which is not part of a sample processing unit and which comprises a stationary rack input device and a stationary rack output device.

5. The apparatus according to claim 1, wherein said second sample transport means further comprises:

(i) a transfer line for transporting said sample racks from the rack supply unit to said rotatable sample rack carrier and from said rotatable sample rack carrier to the rack supply unit, (ii) means for moving serially and one-by-one sample racks from said rack input device to said transfer line, (iii) at the end of each rotation step of said step-wise rotation a selected one of the sample racks is aligned with and is ready to be transferred either a) to said transfer line for transport to said rack output device of said rack supply unit, or b) to a free position on said sample rack carrier aligned with said transfer line for receiving a sample rack from said transfer line, (iv) means for moving a selected sample rack from said transfer line to a free position on said sample rack carrier, during one of said rotation stop intervals, and for moving a selected sample rack from its position on the sample rack carrier to the transfer line, during another one of said rotation stop intervals, (v) means for moving sample racks one-by-one from said transfer line to said rack output device, and (vi) a reader device for reading the identification of each sample rack and the identification of each sample tube contained therein during transport from the rack supply unit to the rotatable sample rack carrier.

6. The apparatus according to claim 5, wherein said transfer line is a single transfer line for transporting said sample racks in two opposite directions, from said rack supply unit to said rotatable sample rack carrier and from said rotatable sample rack carrier to said rack supply unit.

7. The apparatus according to claim 5, wherein said second sample transport means further comprises means for moving a sample rack containing at least one sample that requires urgent analysis from a rack input position to said transfer line in order for that sample rack to be transferred to the rotatable sample rack carrier with high priority.

8. The apparatus according to claim 5, wherein the angle of rotation of the sample rack carrier is such that at the end of each rotation step a selected one of the sample racks on said rotatable sample rack carrier is aligned with and is ready to be transferred to said transfer line for its transport to said rack output device, or a free position on said rotatable sample rack carrier is aligned with said transfer line, said free position being available for receiving a sample rack arriving to said sample rack carrier via said transfer line.

9. The apparatus according to claim 1, wherein said sample tubes are arranged substantially in a row along the length axis of each sample rack.

10. The apparatus according to claim 1, wherein said sample tube area includes space reserved for accommodating one or more sample tube racks manually positioned on a stationary support.

11. The apparatus according to claim 1, wherein said control means are adapted for selecting a rack to be removed from said rotatable sample rack carrier as soon as possible after processing of all sample tubes on said rack is terminated.

12. The apparatus according to claim 1, wherein said control means are adapted for determining the angle of rotation of said rotatable sample rack carrier for each rotation step.

13. An automatic chemical analytical apparatus for analyzing liquid samples comprising:

(a) a plurality of elongated sample racks, each of which has a length axis and accommodates a plurality of sample tubes, each sample tube being filled with a sample, each sample tube carrying on it an identification readable by a reader device and each sample rack carrying on it an identification readable by a reader device, (b) a first sample transport arrangement including a rotatable sample rack carrier located in said sample tube area, said rotatable sample rack carrier accommodating a plurality of said sample racks within a space delimited by a circumference of the carrier, said sample racks being arranged along said circumference with the length axis of each of said sample racks orthogonal to said circumference, said first sample transport arrangement further including a motor for rotating in a step-wise manner said rotatable sample rack carrier, said step-wise rotation comprising rotation intervals and rotation stop intervals, during which said sample rack carrier is at rest, (c) second sample transport arrangement for transporting said sample racks from a rack input device of a rack supply unit to said rotatable sample rack carrier, and for selectively transporting said sample racks from said rotatable sample rack carrier to a rack output device of said rack supply unit, said rack input device and said rack output device each accommodating a plurality of said sample racks, (d) an automatic pipetting unit for aspirating a portion of a sample contained in any sample tube located in any sample rack carried by said sample rack carrier, said aspirating being effected during a rotation stop interval, and for delivering said aspirated sample portion to any reaction tube in a reaction tube area, said automatic pipetting unit comprising a pipetting needle and means for moving said needle in each one of 3 directions (X, Y, Z) which are orthogonal to each other, (e) a controller for controlling and coordinating the operation of said first sample transport arrangement, said second sample transport arrangement, and said automatic pipetting unit, so that a selected sample is delivered to a selected reaction tube; and (f) computer control means which control the operation of said automatic pipetting unit, said first sample transport means, and said second sample transport means, for minimizing the time interval during which each rack occupies a place on said rotatable sample rack carrier.

14. The apparatus according to claim 13, wherein said second sample transport arrangement transports said sample racks one-by-one from said rack input device to said rotatable sample rack carrier.

15. The apparatus according to claim 13, wherein said second sample transport arrangement selectively transports said sample racks one-by-one from said rotatable sample rack carrier to said rack output device.

16. The apparatus according to claim 13, wherein said rack supply unit is a separate module that is not part of a sample processing unit and comprises a stationary rack input device and a stationary rack output device.

17. The apparatus according to claim 13, wherein said second sample transport arrangement further comprises:
(i) a transfer line for transporting said sample racks from the rack supply unit to said rotatable sample rack carrier and from said rotatable sample rack carrier to said rack supply unit,
(ii) means for moving serially and one-by-one sample racks from said rack input device to said transfer line,
(iii) said motor rotating said rotatable sample rack carrier in a step-wise manner so that at the end of each rotation step a selected one of the sample racks is aligned with and is ready to be transferred either
   a) to said transfer line for transport to said rack output device of said rack supply unit, or
   b) to a free position on said sample rack carrier aligned with said transfer line for receiving a sample rack from said transfer line,
(iv) means for moving a selected sample rack from said transfer line to a free position on said sample rack carrier, during one of said rotation stop intervals, and for moving a selected sample rack from its position on the sample rack carrier to the transfer line, during another one of said rotation stop intervals,
(v) means for moving sample racks one-by-one from said transfer line to said rack output device, and
(vi) a reader device for reading the identification of each sample rack and the identification of each sample tube contained therein during transport from the rack supply unit to the rotatable sample rack carrier.

18. The apparatus according to claim 17, wherein said transfer line is a single transfer line for transporting said sample racks in two opposite directions, from said rack supply unit to said rotatable sample rack carrier and from said rotatable sample rack carrier to said rack supply unit.

19. The apparatus according to claim 17, wherein said second sample transport arrangement further comprises means for moving a sample rack containing at least one sample that requires urgent analysis from a rack input position to said transfer line in order for that sample rack to be transferred to the rotatable sample rack carrier with high priority.

20. The apparatus according to claim 17, wherein said second sample transport arrangement further comprises a carriage coupled to a selected sample rack and a transport chain operatively connected to the carriage for moving the carriage and the selected sample rack along the transfer line.

21. The apparatus according to claim 20, wherein said second sample transport arrangement further comprises guiding rolls and a guiding rail positioned adjacent the carriage for guiding the movement of the carriage.

22. The apparatus according to claim 20, wherein said second sample transport arrangement further comprises a chain guide positioned adjacent the transport chain for guiding the movement of the transport chain.

23. The apparatus according to claim 17, wherein the angle of rotation of the sample rack carrier is such that at the end of each rotation step a selected one of the sample racks on said rotatable sample rack carrier is aligned with and is ready to be transferred to said transfer line for its transport to said rack output device, or a free position on said rotatable sample rack carrier is aligned with said transfer line, said free position being available for receiving a sample rack arriving to said sample rack carrier via said transfer line.

24. The apparatus according to claim 13, wherein said sample tubes are arranged substantially in a row along the length axis of each sample rack.

25. The apparatus according to claim 13, wherein said sample tube area includes space reserved for accommodating one or more sample tube racks manually positioned on a stationary support.

26. The apparatus according to claim 13, wherein said control means are adapted for selecting a rack to be removed from said rotatable sample rack carrier as soon as possible after processing of all sample tubes on said rack is terminated.

27. The apparatus according to claim 13, wherein said control means are adapted for determining the angle of rotation of said rotatable sample rack carrier for each rotation step.

* * * * *